United States Patent [19]
Aung et al.

[11] Patent Number: 5,267,567
[45] Date of Patent: Dec. 7, 1993

[54] OSCILLOMETRIC-TYPE BLOOD PRESSURE MEASURING APPARATUS

[75] Inventors: Ye Aung, Komaki; Hideo Nishibayashi, Inuyama, both of Japan

[73] Assignee: Colin Electronics Co., Ltd., Aichi, Japan

[21] Appl. No.: 910,212

[22] Filed: Jul. 9, 1992

[30] Foreign Application Priority Data

Jul. 15, 1991 [JP] Japan ................. 3-200041

[51] Int. Cl.⁵ .............................................. A61B 5/02
[52] U.S. Cl. ............................................... 128/680
[58] Field of Search ........................... 128/677-683, 128/687-690, 672

[56] References Cited

U.S. PATENT DOCUMENTS 4,830,017  5/1989  Perry et al. ................. 128/677
4,928,701  5/1990  Harada et al. ............... 128/681

FOREIGN PATENT DOCUMENTS 0152848  2/1984  European Pat. Off. .

Primary Examiner—Lee S. Cohen
Assistant Examiner—Marianne Parker
Attorney, Agent, or Firm—Oliff & Berridge

[57] ABSTRACT

An oscillometric-type automatic blood pressure measuring apparatus, including a pressure device such as a cuff, an oscillometric-type blood pressure measuring device for (a) occluding an artery of a patient by increasing the cuff pressure, (b) detecting a first pulse wave transmitted from the artery to the cuff by reducing the increased cuff pressure, and (c) determining a first systolic blood pressure of the patient based on variation in amplitude of successive pulses of the first pulse wave, a display for indicating the determined first systolic blood pressure, a detecting device disposed downstream of the cuff, for detecting a second pulse wave produced from a portion of the artery located downstream of the cuff, a first determining device for determining, as an initial-pulse detection pressure, a cuff pressure at the time of detection of an initial pulse of the second pulse wave after the commencement of reduction of the cuff pressure in each of periodic measurement cycles, a second determining device for determining, in a current measurement cycle, a second systolic blood pressure of the patient based on an initial-pulse detection pressure determined in the current cycle and one or more first systolic blood pressures measured in one or more cycles prior to the current cycle, the display means indicating the second systolic blood pressure value before a first systolic blood pressure is determined and displayed in the current cycle.

14 Claims, 5 Drawing Sheets

OSCILLOMETRIC-TYPE BLOOD PRESSURE MEASURING APPARATUS

BACKGROUND OF THE INVENTION

1. Field of the Invention

The present invention relates in general to an oscillometric-type automatic blood pressure measuring apparatus which automatically measures, at predetermined intervals of time, blood pressure of a living subject by the "oscillometric" method.

2. Related Art Statement

There is known an oscillometric-type automatic blood pressure measuring apparatus including (A) pressure means, such as an inflatable cuff, for pressing a body portion of a living subject with a pressure, (B) oscillometric-type blood pressure measuring means operating in each of periodic measurement cycles, for (a) occluding an arterial vessel of the subject by increasing the pressing pressure of the pressure means up to a predetermined target level, (b) detecting a pulse wave transmitted from the arterial vessel to the pressure means by reducing the pressing pressure from the target level, and (c) determining a blood pressure of the subject, such as systolic and/or diastolic blood pressure values, based on time-wise variation of the amplitudes of successive pulses of the pulse wave, and (C) display means for indicating, in each measurement cycle, the determined blood pressure value or values. This apparatus is used for, for example, monitoring the condition of cardiovascular system of a patient during, or after, a surgical operation.

In the above apparatus, the oscillometric-type blood pressure measuring means determines, as a systolic blood pressure of the patient, a pressure of the pressure means at the time of detection of an inflection point (or point of inflection) of the amplitudes of successive pulses of the pulse wave detected by reducing the pressure of the pressure means, which point is located on the upper-pressure side of a pressure of the pressure means (i.e., mean blood pressure of the patient) at the time of detection of a maximum pulse having the greatest amplitude, and further determines as a diastolic blood pressure a pressure of the pressure means at the time of detection of another inflection point of the pulse amplitudes which point is located on the lower-pressure side of the mean blood pressure, and subsequently, the display means indicates the determined blood pressure values on, for example, a cathode ray tube (CRT) thereof. Therefore, it takes a long time, i.e., at least about 20 seconds, to carry out one blood pressure measurement from the commencement of reduction of the pressing pressure of the pressure means to the indication of the blood pressure values on the display means. Thus, this apparatus suffers from a problem that medical staff such as a doctor or nurse cannot quickly read the systolic blood pressure of the patient that is a very important index to be monitored during the surgical operation. It will need more time for the medical staff to read the systolic blood pressure, in the case where a blood pressure measurement is re-started because of, e.g., an insufficiently low target pressure at which the reduction of the pressing pressure is commenced.

Meanwhile, it is possible to determine and display a systolic blood pressure of a subject, when the pressure of the pressure means is reduced to a level equal to a mean blood pressure of the subject and accordingly a maximum pulse having the greatest amplitude is detected. However, the time required for reducing the pressing pressure down to the mean blood pressure is not sufficiently short, and therefore the systolic blood pressure cannot be read so quickly.

It is generally known that, when the pressure of the pressure means is reduced to a level equal to a systolic blood pressure of a subject, blood flow begins to occur in an artery pressed by the pressure means. In the background, the Inventors have found that, when the pressure of the pressure means is reduced to a level equal to, or slightly lower than, a systolic blood pressure of a subject, pulse wave comes to be detectable from a portion of the artery located downstream of the pressure means.

SUMMARY OF THE INVENTION

It is therefore an object of the present invention to provide an oscillometric-type blood pressure measuring apparatus which quickly estimates and displays a systolic blood pressure of a living subject before determining and displaying a proper or true systolic blood pressure of the subject measured by reducing the pressure of the pressure means in accordance with the oscillometric method.

The above object has been achieved by the present invention, which provides an oscillometric-type automatic blood pressure measuring apparatus, comprising (A) pressure means for pressing a body portion of a living subject with a pressure, (B) oscillometric-type blood pressure measuring means operating in each of periodic measurement cycles, for (a) occluding an arterial vessel of the subject by increasing the pressure of the pressure means, (b) detecting a first pulse wave transmitted from the arterial vessel to the pressure means by reducing the increased pressure of the pressure means, and (c) determining a first systolic blood pressure of the subject based on variation in amplitude of successive pulses of the first pulse wave, (C) display means for indicating the first systolic blood pressure value measured by the oscillometric-type blood pressure measuring means, (D) pulse wave detecting means disposed downstream of the pressure means with respect to the arterial vessel, for detecting a second pulse wave produced from a portion of the arterial vessel located downstream of the pressure means, (E) first determining means for determining, as an initial-pulse detection pressure, a pressure of the pressure means at a time when the pulse wave detecting means detects an initial pulse of the second pulse wave after the oscillometric-type blood pressure measuring means commences to reduce the pressure of the pressure means in the each measurement cycle, (F) second determining means for determining, in a current measurement cycle of the oscillometric-type blood pressure measuring means, a second systolic blood pressure of the subject based on an initial-pulse detection pressure determined by the first determining means in the current measurement cycle and at least one first systolic blood pressure measured by the oscillometric-type blood pressure measuring means in at least one measurement cycle prior to the current measurement cycle, and (G) the display means indicating the second systolic blood pressure value determined by the second determining means, before the oscillometric-type blood pressure measuring means determines a first systolic blood pressure value of the subject in the current measurement cycle.

In the oscillometric-type blood pressure measuring apparatus constructed as described above, the pulse wave detecting means is disposed downstream of the pressure means with respect to the arterial vessel, for detecting a second pulse wave produced from a portion of the arterial vessel located downstream of the pressure means, and the first determining means determines, as an initial-pulse detection pressure, a pressure of the pressure means at the time when the pulse wave detecting means detects an initial pulse of the second pulse wave after the oscillometric-type blood pressure measuring means commences the reduction of the pressure of the pressure means in each measurement cycle. The second determining means determines, in a current measurement cycle of the oscillometric-type blood pressure measuring means, a second systolic blood pressure of the subject based on an initial-pulse detection pressure determined by the first determining means in the current measurement cycle and at least one first systolic blood pressure measured by the oscillometric-type blood pressure measuring means in at least one measurement cycle prior to the current measurement cycle, and the display means indicates the second systolic blood pressure value determined by the second determining means, before the oscillometric-type blood pressure measuring means determines a first systolic blood pressure value in the current measurement cycle. Thus, when the pressure of the pressure means is reduced to a level equal to, or slightly lower than, a first systolic blood pressure of the subject, the present apparatus determines and displays a second systolic blood pressure of the subject. Therefore, the present apparatus permits a systolic blood pressure (second systolic blood pressure) to more quickly be read than the conventional apparatus which displays all values such as systolic, mean and diastolic blood pressure values after having detected the time-wise variation of the pulse amplitudes of the pulse wave (first pulse wave), or an apparatus which determines and displays a systolic blood pressure of a subject when the pressure of the pressure means is reduced to a level equal to a mean blood pressure of the subject.

In a preferred embodiment of the present invention, the apparatus further comprises third determining means for determining a pressure difference between the first-pulse detection pressure and the first systolic blood pressure which are determined and measured in the each measurement cycle, the second determining means determining in the current measurement cycle the second systolic blood pressure of the subject based on the initial-pulse detection pressure determined by the first determining means in the current measurement cycle and at least one pressure difference determined by the third determining means in the at least one measurement cycle prior to the current measurement cycle. In this embodiment, the second determining means may determine in the current measurement cycle the second systolic blood pressure of the subject by adding a pressure difference determined by the third determining means in a measurement cycle prior by one cycle to the current measurement cycle, to the initial-pulse detection pressure determined by the first determining means in the current measurement cycle.

In the above embodiment, alternatively, the second determining means may comprise identifying means for identifying a deviation of a pressure difference determined by the third determining means in a measurement cycle prior by one cycle to the current measurement cycle, from at least one pressure difference determined by the third determining means in at least one measurement cycle prior to the one-cycle prior measurement cycle, and adjustment pressure difference determining means for determining an adjustment pressure difference based on the identified deviation and at least one of the pressure difference determined in the one-cycle prior measurement cycle and the at least one pressure difference determined in the at least one measurement cycle prior to the one-cycle prior measurement cycle, the second determining means utilizing the adjustment pressure difference for determining, in the current measurement cycle, the second systolic blood pressure of the subject by adding the adjustment pressure difference to the initial-pulse detection pressure determined by the first determining means in the current measurement cycle. A pressure difference determined by the third determining means in a measurement cycle prior by one cycle to a current measurement cycle, may largely be deviated from at least one pressure difference determined in at least one measurement cycle prior to the one-cycle prior measurement cycle, due to variation of the elevation position of the pulse wave detecting means relative to the heart of the subject, or variation of the distance between the pulse wave detecting means and the pressure means, each of which variations may result from a physical motion of the subject. Even in this case, however, the second determining means identifies the deviation of the pressure difference, determines an adjustment pressure difference based on the identified deviation and at least one of the pressure difference determined in the one-cycle prior measurement cycle and the at least one pressure difference determined in the at least one measurement cycle prior to the one-cycle prior measurement cycle, and utilizes the determined adjustment pressure difference for determining in the current measurement cycle a second systolic blood pressure of the subject by adding the adjustment pressure difference to an initial-pulse detection pressure determined by the first determining means in the current measurement cycle. The second systolic blood pressure thus determined is very reliable.

According to a preferred feature of the present invention, the identifying means of the second determining means comprises means for calculating an arithmetic mean of a first predetermined number of pressure differences determined by the third determining means in a first predetermined number of measurement cycles prior to the one-cycle prior measurement cycle, and means for identifying if the pressure difference determined by the third determining means in the one-cycle prior measurement cycle falls within a deviation range of from a product of the arithmetic mean and a smaller than one and greater than zero value, to a product of the arithmetic mean and a greater than one value, the adjustment pressure difference determining means of the second determining means determining, as the adjustment pressure difference for the current measurement cycle, an arithmetic mean of the pressure difference determined in the one-cycle prior measurement cycle and the first predetermined number of pressure differences determined in the first predetermined number of measurement cycles prior to the one-cycle prior measurement cycle, when the pressure difference determined in the one-cycle prior measurement cycle is identified as falling within the deviation range.

According to another feature of the present invention, the adjustment pressure difference determining means of the second determining means determines, as the adjustment pressure difference for the current measurement cycle, an arithmetic mean of the pressure difference determined in the one-cycle prior measurement cycle and the pressure difference determined in the measurement cycle prior by one cycle to the one-cycle prior measurement cycle, when the pressure difference determined in the one-cycle prior measurement cycle is identified as not falling within the deviation range and simultaneously the pressure difference determined in the measurement cycle prior by one cycle to the one-cycle prior measurement cycle is identified as not falling within a deviation range defined by an arithmetic mean of a first predetermined number of pressure differences determined in a first predetermined number of measurement cycles prior to the measurement cycle prior by one cycle to the one-cycle prior measurement cycle.

According to yet another feature of the present invention, the adjustment pressure difference determining means of the second determining means determines, as the adjustment pressure difference for the current measurement cycle, the adjustment pressure difference determined thereby for the one-cycle prior measurement cycle, when the pressure difference determined in the one-cycle prior measurement cycle is identified as not falling within the deviation range and simultaneously the pressure difference determined in the measurement cycle prior by one cycle to the one-cycle prior measurement cycle is identified as falling within a deviation range defined by an arithmetic mean of a first predetermined number of pressure differences determined in a first predetermined number of measurement cycles prior to the measurement cycle prior by one cycle to the one-cycle prior measurement cycle.

In another embodiment of the present invention, the apparatus further comprises means for determining a first pulse rate of the subject based on at least two successive pulses of the second pulse wave detected by the pulse wave detecting means before the oscillometric-type blood pressure measuring means commences to increase the pressure of the pressure means in the each measurement cycle, means for determining a second pulse rate of the subject based on (a) the initial pulse of the second pulse wave detected by the pulse wave detecting means after the oscillometric-type blood pressure measuring means commences to reduce the pressure of the pressure means in the each measurement cycle and (b) a pulse following the initial pulse, and means for identifying if the second pulse rate falls within a deviation range of from a product of the first pulse rate and a smaller than one and greater than zero value, to a product of the first pulse rate and a greater than one value. In this case, the second determining means utilizes the initial-pulse detection pressure for determining the second systolic blood pressure of the subject, when the second pulse rate is identified as falling within the deviation range, and discarding the initial pulse as a noise when the second pulse rate is identified as not falling within the deviation range. Also, the third determining means utilizes the initial-pulse detection pressure for determining the pressure difference, when the second pulse rate is identified as falling within the deviation range, and discarding the initial pulse as a noise when the second pulse rate is identified as not falling within the deviation range.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
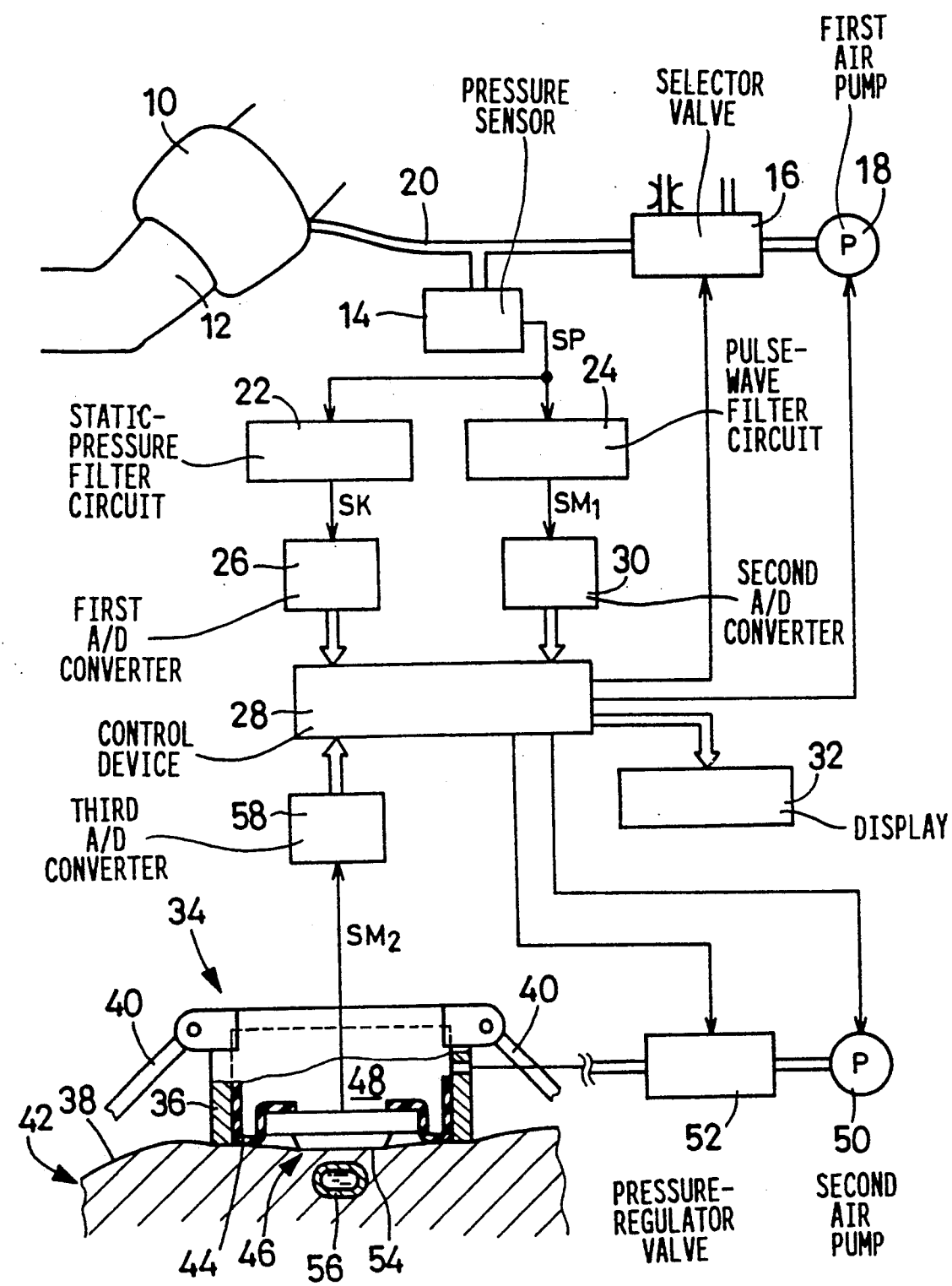
FIG. 1 is a diagrammatic view of an oscillometric-type blood pressure measuring apparatus in accordance with the present invention.

Referring first to FIG. 1, there is shown an oscillometric-type blood pressure measuring apparatus to which the present invention is applied. The apparatus is used for, for example, monitoring the condition of cardiovascular system of a patient during a surgical operation. In the figure, reference numeral 10 designates a bag-like, inflatable cuff formed of rubber. The cuff 10 serves as pressure means for the present embodiment. The cuff 10 is worn on the patient by being wound around an upper arm 12 of the patient. A pressure sensor 14, a selector valve 16, and a first air pump 18 are connected to the cuff 10 via piping 20.

The selector valve 16 is selectively placed in an INFLATION position, a SLOW-DEFLATION position, and a QUICK-DEFLATION position. In the INFLATION position, the selector valve 16 permits pressurized air to be supplied from the first air pump 18 to the cuff 10; in the SLOW-DEFLATION position, the selector valve 16 permits the pressurized air to slowly be discharged from the cuff 10 to the atmosphere; and, in the QUICK-DEFLATION position, the selector valve 16 permits the pressurized air to quickly be discharged from the cuff 10 to the atmosphere.

The pressure sensor 14 detects the air pressure in the cuff 10, and supplies an electric signal, SP, representative of the detected cuff pressure, to a static-pressure filter circuit 22 and a pulse-wave filter circuit 24. The static-pressure filter circuit 22 includes a low-pass filter, that is, a high-frequency cutting filter that cuts off high-frequency components from the pressure signal SP. Stated differently, the filter circuit 22 transmits only a static-pressure signal component ("direct current" component) of the pressure signal SP. Hereinafter, the static-pressure signal component is referred to as the "cuff pressure signal SK". The cuff pressure signal SK is representative of a static pressure, P, in the cuff 10 (hereinafter, referred to as the "cuff pressure P"). The cuff pressure signal SK is supplied to a control device 28 via a first analog to digital (A/D) converter 26.

The pulse-wave filter circuit 24 includes a band-pass filter which has a specific band of frequencies including the frequency of an oscillatory component ("alternating current" component) of the pressure signal SP which component is produced in synchronism with heartbeat of the patient, and transmits only the oscillatory signal component to the control device 28 via a second A/D converter 30. Hereinafter, the oscillatory signal component is referred to as the "cuff pulse wave signal $SM_1$". The cuff pulse wave signal $SM_1$ is representative of the oscillatory pressure wave (i.e., pulse wave) transmitted to the cuff 10 from a brachial artery (not shown) running in the upper arm when the cuff pressure P is slowly reduced.

The control device 28 includes a "microcomputer" constituted by a central processing unit (CPU), a read only memory (ROM), a random access memory (RAM), and an input and output (I/O) port. The CPU processes supplied signals according to control programs pre-stored in the ROM by utilizing the temporary-storage function of the RAM. More specifically, the CPU supplies drive signals to the first air pump 18 and the selector valve 16 via the I/O port and respective drive circuits (not shown), so as to regulate the cuff pressure P. Furthermore, the CPU determines a systolic blood pressure, SYS, a diastolic blood pressure, DIA, and a mean blood pressure, MEAN, of the patient, based on variation in amplitude of successive pulses of the cuff pulse wave signal $SM_1$ and the cuff pressure signal SK obtained by reducing the cuff pressure P from a predetermined target level, $P_m$. The CPU commands a display 32 such as a cathode ray tube (CRT), to indicate the determined blood pressure values SYS, DIA, MEAN. The control programs stored in the ROM include a well-known oscillometric blood pressure measurement algorithm. The CPU operates for carrying out a blood pressure measurement in each of periodic cycles which lasts for a predetermined interval of time, $\alpha$.

As shown in FIG. 1, the present apparatus further includes a pulse wave sensor probe 34. The sensor probe 34 is worn on a wrist 42 of the same superior limb of the patient as that on which the cuff 10 is worn. The sensor probe 32 serves as pulse wave detecting means for the present embodiment. More specifically, the sensor probe 34 is detachably set on a body surface 38 of the wrist 42 with a pair of bands 40, 40 being fastened around the wrist 42, such that an open end of a container-like housing 36 of the sensor probe 34 contacts the body surface 38. A pulse wave sensor 46 is supported by the housing 36 via an elastic diaphragm 44, such that the pulse wave sensor 46 is displaceable relative to the housing 36, when the diaphragm 44 is inflated, so as to be advanceable out of the open end of the housing 36. The housing 36, the diaphragm 44, and the pulse wave sensor 46 cooperate with each other to define a pressure chamber 48, to which pressurized air is supplied from a second air pump 50 via a pressure-regulator valve 52. Thus, the pulse wave sensor 46 is pressed against the body surface 38 with a pressing force corresponding to an air pressure in the pressure chamber 48.

The pulse wave sensor 46 includes at least one semiconductor pressure-sensing element (not shown) which is provided in one of opposite surfaces of a semiconductor substrate, such as a monocrystalline silicon, which one surface provides a press surface 54 of the sensor 46. The pulse wave sensor 46 is pressed against the body surface 38 of the wrist 42, and detects the oscillatory pressure wave (i.e., pulse wave) transmitted to the press surface 54 from a radial artery 56 in synchronism with heartbeat of the patient. The radial artery 56 is a portion of the brachial artery pressed by the cuff 10, and is located downstream of the cuff 10. The pulse wave sensor 46 generates a probe pulse wave signal, $SM_2$, representative of the detected pulse wave. The probe pulse wave signal $SM_2$ is supplied to the control device 28 via a third A/D converter 58. In the present embodiment, the brachial artery is an arterial vessel occluded by the pressure means, and the radial artery 56 is a portion of the arterial vessel located downstream of the pressure means.

The control device 28 operates according to the control programs stored in the ROM, for supplying drive signals to the second air pump 50 and the pressure-regulator valve 52 via respective drive circuits (not shown), so as to regulate the air pressure in the pressure chamber 48. While slowly increasing the pressure in the chamber 48, the control device 28 collects the probe pulse wave signal $SM_2$ supplied from the pulse wave sensor 46 and, based on the collected signal $SM_2$, determines an optimum air pressure (i.e., optimum pressing force) to be applied to the pulse wave sensor 46. More specifically, the control device 28 determines, as the optimum air pressure, an air pressure at the time when the wall of radial artery 56 is partially flattened under the pressing force of the pulse wave sensor 46. The control device 28 controls the pressure-regulator valve 52 so as to maintain the air pressure in the chamber 48 at the determined optimum pressure level.

In addition, while slowly reducing the cuff pressure P, the control device 28 determines, as an initial-pulse detection pressure, $P_s$, a cuff pressure P at the time when the pulse wave sensor 46 detects an initial pulse of the pulse wave produced from the radial artery 56 (i.e., initial pulse of the probe pulse wave signal $SM_2$) after the commencement of reduction of the cuff pressure P. Furthermore, the control device 28 calculates a pressure difference, $\Delta P$, between the initial-pulse detection pressure $P_s$, and a systolic blood pressure SYS determined based on variation of the pulse amplitudes of the cuff pulse wave signal $SM_1$ obtained during the reduction of the cuff pressure P. Also, the control device 28 identifies a deviation of a pressure difference $\Delta P_0$ determined in a current measurement cycle, from one or more pressure differences respectively determined in one or more measurement cycles prior to the current cycle. By utilizing the thus identified deviation, the control device 28 determines an adjustment pressure difference, $\Delta P'$.

According to the control programs stored in the ROM, the control device 28 estimates a systolic blood pressure, SYS', of the patient by adding to an initial-pulse detection pressure $P_s$ determined in a current measurement cycle an adjustment pressure difference $\Delta P'$ determined in a measurement cycle prior by one cycle to the current measurement cycle, and commands the display 32 to indicate the estimated systolic blood pressure SYS' before a proper or true systolic blood pressure SYS is determined or displayed in the current cycle. In the present embodiment, the control device 28 serve as means for determining an initial-pulse detection pressure $P_s$, means for determining a pressure difference $\Delta P$ between an initial-pulse detection pressure $P_s$ and a systolic blood pressure determining a systolic blood pressure SYS', and means for determining an adjustment pressure difference $\Delta P'$.

Figure 2:
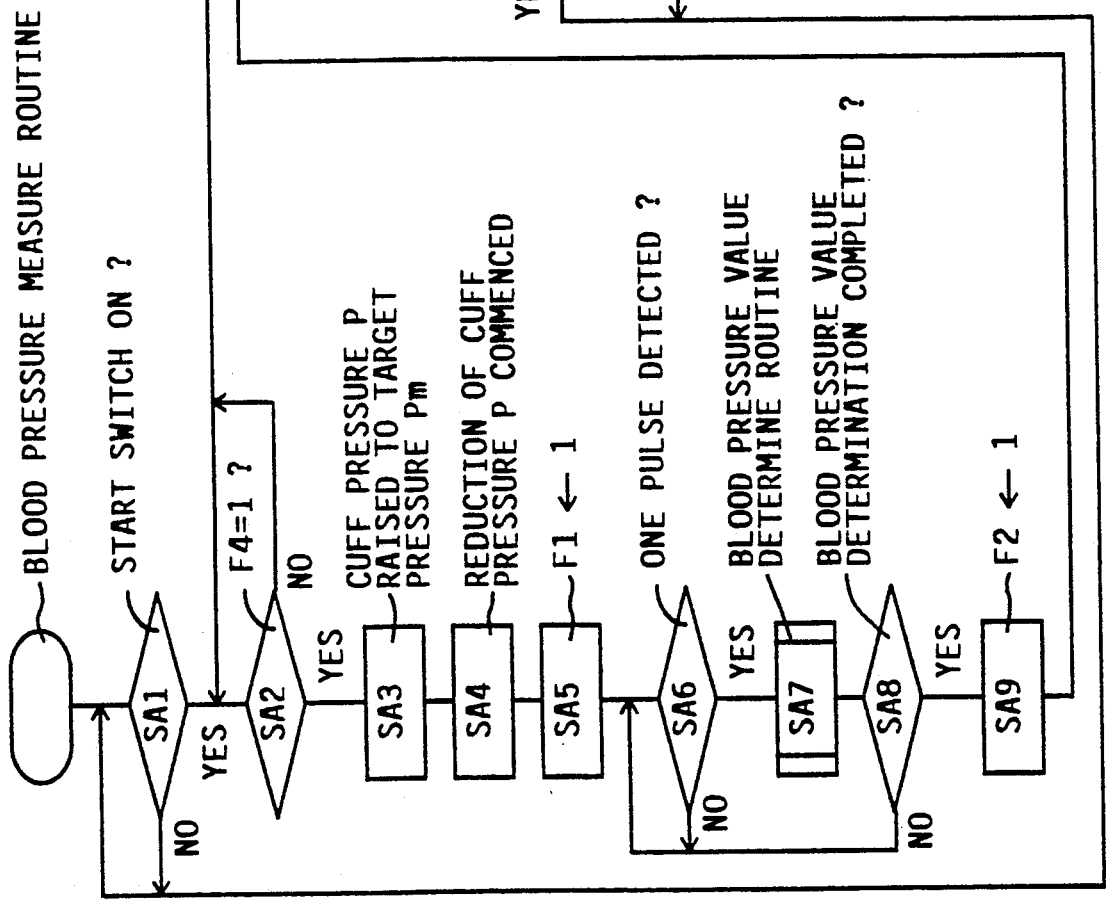
FIG. 2 is a flow chart representing the blood pressure measure routine as a part of the operation of the apparatus of FIG. 1.
Figure 3A:
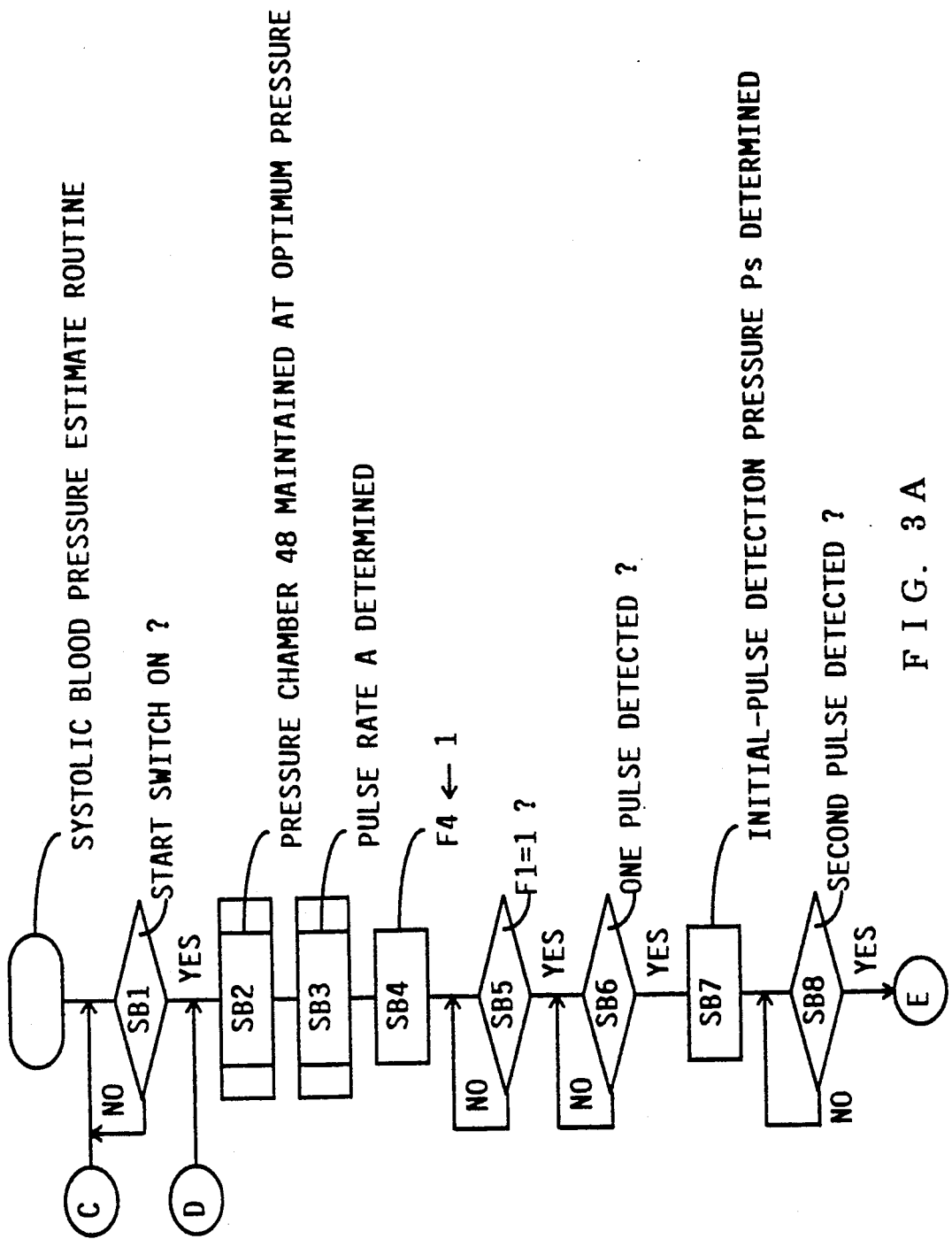
FIG. 3 (FIGS. 3A, 3B, and 3C) is a flow chart illustrating the systolic blood pressure estimate routine as another part of the operation of the apparatus of FIG. 1, which routine is carried out in parallel with the routine of FIG. 2.
Figure 3B:
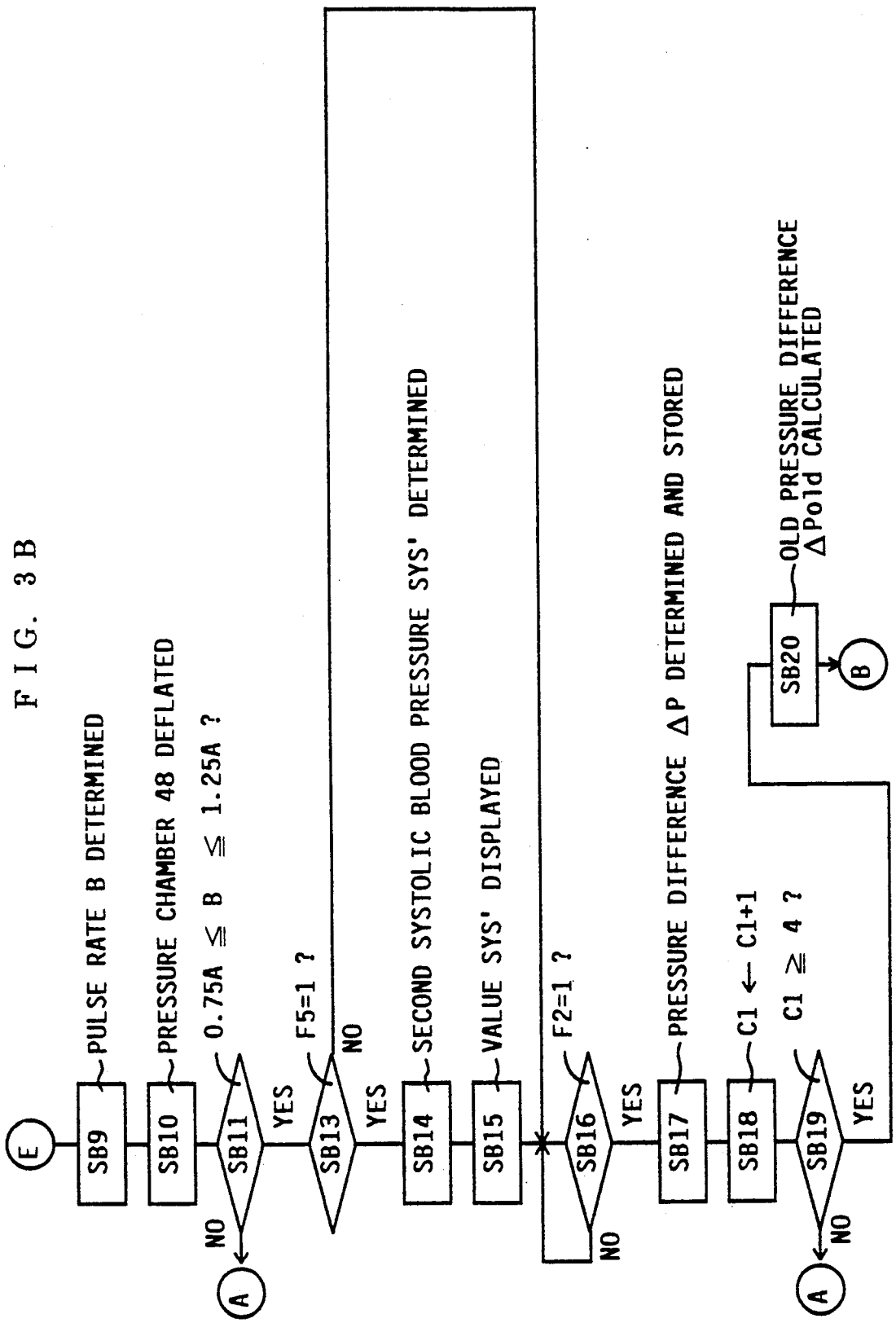
Figure 3C:
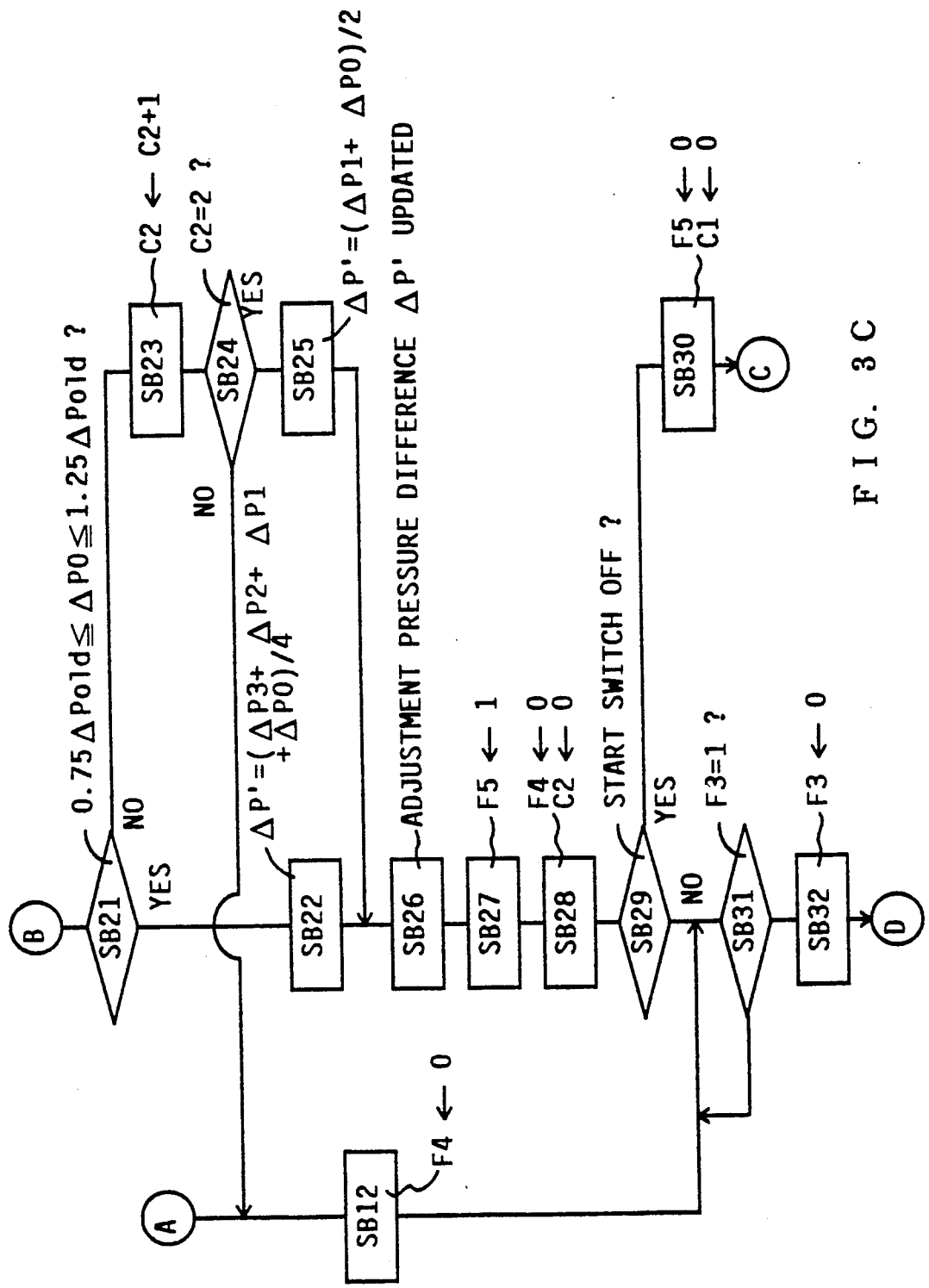

Hereinafter, there will be described the operation of the oscillometric-type blood pressure measuring apparatus constructed as described above, by reference to the flow charts of FIG. 2 and FIG. 3 (FIGS. 3A, 3B, and 3C).

First, upon application of electric power to the present system, an initialization step (not shown) is carried out. Subsequently, the CPU carries out the blood pressure measure routine of FIG. 2 and the systolic blood pressure estimate routine of FIG. 3, in parallel with each other.

In Step SA1 of FIG. 2, the CPU judges whether or not a START switch (not shown) has been turned ON. When a negative judgement (NO) is made in Step SA1, the CPU repeats this step, waiting for an affirmative judgement (YES). When an affirmative judgement is made in this step, the control of the CPU goes to Step SA2 to judge whether or not a fourth flag, $F_4$, is in a state, $F_4=1$. The state $F_4=1$ of the fourth flag $F_4$ indicates that a pulse rate, A, of the patient has been determined based on the probe pulse wave signal $SM_2$ in the systolic blood pressure estimate routine (FIG. 3, described later). If a negative judgement is made in Step SA2, the CPU repeats this step, waiting for an affirmative judgement. Meanwhile, if the fourth flag $F_4$ is in the state $F_{4=1}$ and therefore an affirmative judgement is provided in this step, the control of the CPU goes to Step SA3 to place the selector valve 16 at the INFLATION position and actuates the first air pump 18 so as to supply pressurized air to the cuff 10 and increase the cuff pressure P up to a target pressure level $P_m$ (e.g., about 180 mmHg) higher by a suitable amount than an estimated systolic blood pressure of the patient. Thus, the cuff pressure P, represented by the cuff pressure signal SK, is increased to the target level $P_m$. Step SA3 is followed by Step SA4 to stop the first air pump 18 and switch the selector valve 16 from the INFLATION position to the SLOW-DEFLATION position, so as to commence reduction of the cuff pressure P. In the following Step SA5, the CPU places a first flag, $F_1$, in a state, $F_1=1$. The state $F_1=1$ of the first flag $F_1$ indicates that the cuff pressure P is being reduced slowly.

During the slow reduction of the cuff pressure P, Step SA6 is carried out to judge whether or not one pulse of the cuff pulse wave signal $SM_1$ corresponding to one heartbeat of the patient has been supplied from the cuff 10 (or pulse-wave filter circuit 24). In the present embodiment, the supplied signal $SM_1$ is subjected to a well-known median filter treatment to remove noise mixed therewith, and in the case where noise cannot completely be removed by the median filter treatment, the signal $SM_1$ including noise is discarded. If a negative judgement is made in Step SA6, the CPU repeats this step. Meanwhile, if an affirmative judgement is made in the step, the control of the CPU goes to Step SA7, i.e., blood pressure value determine routine. In this sub-routine, the CPU 24 determines a systolic blood pressure SYS, a diastolic blood pressure DIA, and a mean blood pressure MEAN of the patient, based on time-wise variation of the amplitudes of successive pulses of the cuff pulse wave signal $SM_1$ obtained during the slow reduction of the cuff pressure P. More specifically, the CPU 24 determines as the mean blood pressure MEAN a cuff pressure P at the time of detection of a maximum pulse of the signal $SM_1$ which pulse has the greatest amplitude, determines as the systolic blood pressure SYS a cuff pressure P at the time of detection of an inflection point (or point of inflection) of the pulse amplitudes of the cuff pulse wave signal $SM_1$ which point is located on the upper-pressure side of the mean blood pressure MEAN, and further determines as the diastolic blood pressure DIA a cuff pressure P at the time of detection of another inflection point of the pulse amplitudes which point is located on the lower-pressure side of the mean blood pressure MEAN.

Step SA7 is followed by Step SA8 to judge whether or not the blood pressure value determination in Step SA7 has been completed. When a negative judgement is made in Step SA8, the CPU 24 repeats Step SA6 to Step SA8. Meanwhile, if an affirmative judgement is made in Step SA8, the control of the CPU goes to Step SA9 to place a second flag, $F_2$, in a state, $F_2=1$, indicating that the blood pressure value determine routine of Step SA7 has been completed.

Step SA9 is followed by Step SA10 to command the CRT display 32 to indicate the determined values SYS, DIA, MEAN thereon. In the following Step SA11, the CPU switches the selector valve 16 from the SLOW-DEFLATION position to the QUICK-DEFLATION position, thereby quickly reducing the cuff pressure P. Then, in Step SA12, the CPU resets the first flag $F_1$ to zero. Step SA12 is followed by Step SA13 to judge whether or not the START switch has been turn OFF to stop the operation of the present apparatus. If an affirmative judgement is made in Step SA13, the control of the CPU goes back to Step SA1 and waits. On the other hand, if a negative judgement is made in Step SA13, the control goes to Step SA14 to judge whether or not a predetermined interval of time, $\alpha$, has elapsed after the initialization of the apparatus. For example, the interval time $\alpha$ is pre-determined at 5 to 10 minutes.

If a negative judgement is made in Step SA14, then the CPU repeats this step. Meanwhile, when the interval time $\alpha$ has elapsed and an affirmative judgement is made in Step SA14, the control of the CPU 24 goes to Step SA15 to place a third flag, $F_3$, in a state, $F_3=1$, indicating that the interval time $\alpha$ has elapsed. Step SA15 is followed by Step SA16 to reset the second flag $F_2$ to zero, and then the control of the CPU goes back to Step SA2. Thus, the present apparatus carries out the blood pressure measure routine of FIG. 2 in each of the periodic measurement cycles, at the predetermined interval $\alpha$, and displays the blood pressure values SYS, DIA, MEAN on the display 32 in each cycle.

Referring next to FIG. 3 (FIGS. 3A, 3B, and 3C), there will be described the systolic blood pressure estimate routine. First, in Step SB1, the CPU judges whether or not the START switch of the apparatus has been turned ON. If a negative judgement is made in Step SB1, the CPU repeats this step. Meanwhile, if an affirmative judgement is made in this step, the control of the CPU goes to Step SB2 to determine an optimum air pressure (or optimum pressing force) to be applied to the pressure chamber 48 of the pulse wave sensor probe 34 and maintain the air pressure of the pressure chamber 48 at the determined optimum pressure level.

Step SB2 is followed by Step SB3 to determine a period of generation of the successive pulses of the probe pulse wave signal $SM_2$, based on two successive pulses of the signal $SM_2$ before the cuff pressure P is increased in the blood pressure measure routine (FIG. 2). In this step, the CPU calculates a pulse rate (i.e., number of pulses per minute), A, of the patient by dividing 60 seconds by the determined period, and stores data indicative of the pulse rate A in the RAM. Step SB3 is followed by Step SB4 to place the fourth flag $F_4$ in the state $F_4=1$ indicating that the pulse rate A has been determined.

Subsequently, in Step SB5, the CPU judges whether or not the first flag $F_1$ is in the state $F_1=1$, that is, the cuff pressure P is being reduced slowly. If a negative judgement is made in this step, the CPU repeats this step. Meanwhile, if an affirmative judgement is made in Step SB5, the control of the CPU goes to Step SB6 to judge whether or not one pulse of the signal $SM_2$ corresponding to one heartbeat of the patient has been supplied from the pulse wave sensor 46. As long as the judgement in Step SB6 remains negative, the CPU continues to repeat the step. If an affirmative judgement is made in this step, the control of the CPU goes to Step SB7 to determine, as an initial-pulse detection pressure $P_s$, a cuff pressure P at the time of detection of an initial pulse of the signal $SM_2$ that is the first pulse supplied from the pulse wave sensor 46 after the commencement of reduction of the cuff pressure P, and store data indicative of the initial-pulse detection pressure $P_s$ in the RAM.

Step S7 is followed by Step S8 to judge whether or not another (second) pulse of the signal $SM_2$ has been supplied following the initial (first) pulse. If a negative judgement is made in Step SB8, the CPU repeats this step. Meanwhile, if an affirmative judgement is made in Step SB8, the control of the CPU goes to Step SB9 to determine, in the same manner as that described above with respect to the pulse rate A (Step SB3), a pulse rate, B, of the patient based on the initial (first) and following (second) pulses obtained in Steps SB6 and SB8, respectively, during the reduction of the cuff pressure P. Step SB9 is followed by Step SB10 to discharge the pressurized air from the pressure chamber 48.

Subsequently, in Step SB11, the CPU judges whether or not the pulse rate B obtained during the reduction of the cuff pressure P falls within the range of from 75% to 125% of the pulse rate A (i.e., $0.75A \leq B \leq 1.25A$). A negative judgement in Step SB11 indicates that the initial (first) pulse obtained in Step SB6 is not a true pulse but a noise. In this case, the control of the CPU goes to Step SB12 to reset the fourth flag $F_4$ to zero. Step SB12 is followed by Step SB31 to judge whether or not the third flag $F_3$ is in the state $F_3 = 1$ indicating that the measurement interval time $\alpha$ has elapsed. As long as the judgement in Step SB31 remains negative, the CPU continues to repeat this step. Meanwhile, if an affirmative judgement is made in Step SB31, and another blood pressure measurement is started, the control of the CPU goes to Step SB32 to reset the third flag $F_3$ to zero, and then goes back to Step SB2.

On the other hand, an affirmative decision in Step SB11 indicates that the initial pulse obtained in Step SB6 is not a noise but a true or proper pulse representative of the heartbeat-synchronous pulse wave transmitted from the radial artery 56. Therefore, the control of the CPU proceeds with Step SB13 and the following steps. In Step SB13, the CPU decides whether or not a fifth flag, $F_5$, is in a state, $F_5 = 1$, indicating that the stored data indicative of the adjustment pressure difference $\Delta P'$ has been updated (described in detail later). In the initial or first blood pressure measurement cycle, the adjustment pressure difference $\Delta P'$ has not been determined yet, and a negative decision is made in Step SB13. Thus, the CPU bypasses Steps SB14 and SB15 and goes to Step SB16 to judge whether or not the second flag $F_2$ is in the state $F_2 = 1$ indicating that the blood pressure values have been determined in Step SA7 (FIG. 2). If a negative judgement is made in Step SB16, the CPU repeats this step. Meanwhile, if an affirmative judgement is made in Step SB16, the control goes to SB17 to calculate, and store, a pressure difference $\Delta P$ between the systolic blood pressure SYS determined in Step SA7 (hereinafter, referred to as the "first systolic blood pressure SYS") and the initial-pulse detection pressure $P_s$ determined in Step SB7.

Step SB17 is followed by Step SB18 to add one to the content of a first counter, $C_1$, which counts the number of the pressure differences $\Delta P$ calculated in Step SB17 in respective cycles. Subsequently, in Step SB19, the CPU identifies whether or not the number counted by the first counter $C_1$ is not less than four. If a negative result is provided in Step SB19, the CPU goes to Step SB12 and then Step S31. On the other hand, if four or more pressure differences $\Delta P$ have been obtained and an affirmative result is given in Step SB19, the control of the CPU goes to Step SB20.

In Step SB20, the CPU calculates, as an old pressure difference, $\Delta P_{old}$, an arithmetic mean of the three pressure differences $\Delta P_1$, $\Delta P_2$, $\Delta P_3$ obtained in the three measurement cycles respectively prior by one, two and three cycles to the current measurement cycle in which the pressure difference $\Delta P_0$ has been obtained in Step SB17. In this connection, a measurement cycle in which a pressure difference $\Delta P$ is not determined, is not counted or considered. Step SB20 is followed by Step SB21 to identify whether or not the pressure difference $\Delta P_0$ obtained in the current cycle falls within the range of from 75% to 125% of the old pressure difference $\Delta P_{old}$ (i.e., $0.75\Delta P_{old} \leq \Delta P_0 \leq 1.25\Delta P_{old}$). If an affirmative result is obtained in Step SB21, the CPU goes to Step SB22 to calculate, as an adjustment pressure difference $\Delta P'$, an arithmetic mean of the four pressure differences $\Delta P_0$, $\Delta P_1$, $\Delta P_2$, $\Delta P_3$. On the other hand, if a negative result is provided in Step SB21, that is, if it is identified that the pressure difference $\Delta P_0$ obtained in the current cycle is significantly largely deviated from the old pressure difference $\Delta P_{old}$, the control of the CPU goes to Step SB23 to add one to a second counter, $C_2$, which counts the number of the negative results provided in Step SB21 in respective cycles. Step SB23 is followed by Step SB24 to judge whether or not the number counted by the second counter $C_2$ is two, that is, negative results have been provided in Step SB21 in successive two cycles, respectively.

If a negative judgement is made in Step SB24, the CPU goes to Step SB12 and then Step SB31. On the other hand, if an affirmative judgement is made in Step SB24, the CPU goes to Step SB25 to calculate, as an adjustment pressure difference $\Delta P'$, an arithmetic mean of the two pressure differences $\Delta P_0$, $\Delta P_1$. In the present embodiment, Steps SB21, SB23, and SB24 and a portion of the microcomputer for effecting these steps cooperate with each other to serve as identifying means for identifying a deviation of a pressure difference determined in an arbitrary measurement cycle, from at least one pressure difference determined in at least one measurement cycle prior to that measurement cycle; and Steps SB22 and SB25 and a portion of the microcomputer for effecting these steps cooperate with each other to serve as adjustment pressure difference determining means for determining an adjustment pressure difference based on the identified deviation and at least one of the pressure difference determined in that measurement cycle and the at least one pressure difference determined in the at least one measurement cycle prior to that measurement cycle.

If an adjustment pressure difference $\Delta P'$ is determined in Step SB22 or SB25, the control of the CPU goes to Step SB26 to update the adjustment pressure difference $\Delta P'$ by replacing the old one with the new one. Step SB26 is followed by Step SB27 to place the fifth flag $F_5$ in the state $F_5=1$, and subsequently by Step SB28 to reset the fourth flag $F_4$ and the second counter $C_2$ each to zero. Step SB28 is followed by Step SB29 to judge whether or not the START switch has been turned OFF. If an affirmative judgement is made in Step SB29, the CPU goes to Step SB30 to reset the fifth flag $F_5$ and the first counter $C_1$ each to zero and clear the stored data indicative of the pressure differences $\Delta P_0$, $\Delta P_1$, $\Delta P_2$, $\Delta P_3$, etc. Then, the CPU goes back to Step SB1, and waits for another operation of the START switch.

On the other hand, if a negative judgement is made in Step SB29, the CPU goes to Step SB31 to judge whether or not the third flag $F_3$ is in the state $F_3=1$ indicating that the measurement interval time $\alpha$ has elapsed. As long as the judgement in Step SB31 remains negative, the CPU continues to repeat this step. On the other hand, if an affirmative judgement is made in Step SB31 and another blood pressure measurement has been started, the CPU goes to Step SB32 to reset the third flag $F_3$ to zero, and then goes back to Step SB2.

In the case where the adjustment pressure difference $\Delta P'$ is updated in Step SB26, an affirmative judgement is made in Step SB13 and therefore, in the following Step SB14, the CPU determines a systolic blood pressure SYS' (hereinafter, referred to as the "second systolic blood pressure SYS'") by adding to the initial-pulse detection pressure $P_s$ determined in the current measurement cycle the adjustment pressure difference $\Delta P'$ updated or determined in the measurement cycle preceding (i.e., prior by one cycle to) the current measurement cycle. Step SB14 is followed by Step SB15 to indicate the determined second systolic blood pressure SYS' on the display 32 before the first systolic blood pressure SYS is determined in Step SA7 and indicated on the display 32. Subsequently, the adjustment pressure difference $\Delta P'$ used in Step SB14 in the current measurement cycle is updated in Step SB26 as described above, so that the thus updated value $\Delta P'$ is used in a measurement cycle following the current measurement cycle. Thus, each time a blood pressure measurement is carried out in each periodic cycle, a second systolic blood pressure SYS' is determined based on (a) an initial-pulse detection pressure $P_s$ determined in a current measurement cycle and (b) an adjustment pressure difference $\Delta P'$ determined in a measurement cycle preceding the current cycle (if a negative judgement is made in Step SB24, not the value $\Delta P'$ determined in the preceding cycle, but a value $\Delta P'$ determined in a measurement cycle prior by two cycles to the current cycle), and the determined second systolic blood pressure SYS' is indicated on the display 32 before the first systolic blood pressure SYS is determined or displayed.

As emerges from the foregoing description, the present blood pressure measuring apparatus determines, in the systolic blood pressure estimate routine (FIG. 3), a second systolic blood pressure SYS' by adding an adjustment pressure difference $\Delta P'$ to an initial-pulse detection pressure $P_s$, that is, a cuff pressure P at the time when, during the reduction of the cuff pressure P, an initial pulse of the pulse wave is detected from the radial artery 56 that is a distal portion of the brachial artery extending in the upper arm 12 pressed by the cuff 10. The apparatus indicates the determined value SYS' on the display 32, before determining or indicating the first systolic blood pressure SYS in the blood pressure measure routine (FIG. 2) in the same or common measurement cycle. The initial-pulse detection pressure $P_s$ is equal to, or slightly lower than, the first systolic blood pressure SYS, and the present apparatus determines and displays the second systolic blood pressure SYS' immediately after determining the initial-pulse detection pressure $P_s$. Therefore, the apparatus permits a systolic blood pressure (second systolic blood pressure SYS') to more quickly be read by medical staff than the conventional apparatus which determines and displays all values such as systolic, mean, and diastolic blood pressure values SYS, MEAN, DIA after having detected the time-wise variation of the pulse amplitudes of the pulse wave (cuff pulse wave signal $SM_1$), or an apparatus which determines and displays a systolic blood pressure of a patient when the cuff pressure P is reduced to a level equal to a mean blood pressure of the patient.

In addition, the present apparatus identifies a deviation of the pressure difference $\Delta P_0$ determined in a current measurement cycle, from the old pressure difference $\Delta P_{old}$, that is, arithmetic average of the three pressure differences $\Delta P_1$, $\Delta P_2$, $\Delta P_3$ respectively determined in the three measurement cycles prior to the current cycle, and determines an adjustment pressure difference $\Delta P'$ based on the identified deviation and two or all of the four pressure differences $\Delta P_0$, $\Delta P_1$, $\Delta P_2$, $\Delta P_3$. This adjustment pressure difference $\Delta P'$ is utilized for determining a second systolic blood pressure SYS'. Therefore, even in the case where the pressure differences $\Delta P$ may largely vary due to variation of the elevation position of the pulse wave sensor 46 relative to the heart of the patient, or variation of the distance between the pulse wave sensor 46 and the cuff 10 because of displacement of either or both thereof, each of which variations may result from a physical motion of the patient, the present apparatus provides the second systolic blood pressure SYS' with high reliability. More specifically, in the case where a pressure difference $\Delta P_0$ determined in a current measurement cycle is not significantly largely deviated from an old pressure difference $\Delta P_{old}$, an arithmetic average of the four pressure differences $\Delta P_0$, $\Delta P_1$, $\Delta P_2$, $\Delta P_3$ is determined as an adjustment pressure difference $\Delta P'$. Meanwhile, in the case where a pressure difference $\Delta P_0$ is significantly largely deviated from an old pressure difference $\Delta P_{old}$ in each of two successive measurement cycles, an arithmetic average of the two pressure differences $\Delta P_0$, i.e., values $\Delta P_0$ and $\Delta P_1$ as counted in the latter cycle out of the two successive cycles, is determined as an adjustment pressure difference $\Delta P'$. Since the adjustment pressure difference $\Delta P'$ is determined by utilizing the deviation of the pressure difference $\Delta P_0$ and the second systolic blood pressure value SYS' is determined by utilizing the thus determined value $\Delta P'$, the present apparatus determines the second systolic blood pressure SYS' with various advantages, for example, irrespective of the physical activity or motion of the patient.

Furthermore, the present apparatus identifies whether or not an initial pulse detected through the pulse wave sensor 46 during the reduction of the cuff pressure P is a noise, by comparing the pulse rate B determined based on the initial pulse and the second pulse following the initial pulse, with the pulse rate A determined before the inflation of the cuff 10 is commenced. In the case where the initial pulse is identified as being a noise in a measurement cycle, the apparatus does not determine a second systolic blood pressure SYS', calculate a pressure difference $\Delta P$, nor determine an adjustment pressure difference $\Delta P'$, in the measurement cycle. Thus, the reliability of the second systolic blood pressure values SYS' is improved.

While the present invention has been described in detail in its preferred embodiment, it is to be understood that the present invention is by no means limited to the illustrated details of the preferred embodiment.

For example, although in the illustrated embodiment the second systolic blood pressure values SYS' is determined by using the adjustment pressure difference $\Delta P'$, it is possible to determine the value SYS' by adding, in place of the value $\Delta P'$, a pressure difference $\Delta P$ determined in a measurement cycle prior by one cycle to a current measurement cycle, to an initial-pulse detection pressure $P_s$ determined in the current cycle. In this case, Steps SB18 through SB26 are omitted from the flow chart of FIG. 3. This apparatus is also capable of displaying the second systolic value SYS' before determining and displaying a first systolic blood pressure SYS in the current cycle.

While in the illustrated embodiment the adjustment pressure difference $\Delta P'$ is determined in Step SB22 based on the four pressure differences $\Delta P_0$, $\Delta P_1$, $\Delta P_2$, $\Delta P_3$, it is possible to determine the value $\Delta P'$ based on three, five or other number of pressure difference values $\Delta P$.

The illustrated blood pressure measuring apparatus may be adapted to correct the first systolic blood pressure value SYS by utilizing the second systolic blood pressure value SYS', and display the corrected first systolic blood pressure value.

In the illustrated apparatus, pulse wave may be detected through the pulse wave sensor 46 at the time of commencement of the slow reduction of the cuff pressure P, due to an insufficiently low target pressure $P_m$, and a determined second systolic blood pressure value SYS' may be higher than a predetermined target pressure $P_m$, due to detection of a noise as an initial pulse. The apparatus may be adapted to raise, in those cases, the cuff pressure P to a different target pressure higher than the pressure level $P_m$, and re-start a blood pressure measurement.

While in the illustrated embodiment the pulse wave sensor probe 34 (or pulse wave sensor 36) for detecting pressure pulse wave is used as the pulse wave detecting means, it is possible to use, as the pulse wave detecting means, an oximeter probe (or oximeter) for detecting a photoelectric pulse wave from an artery of a subject.

In addition to, or in place of, the CRT display 32 employed in the illustrated embodiment, it is possible to use other sorts of display devices such as a printer.

In the illustrated embodiment, the cuff 10 as the pressure means is set on an upper arm 12 of a patient and the pulse wave sensor probe 34 as the pulse wave detecting means is set on a wrist 38 of the same limb as that on which the cuff 10 is set. However, it is possible to set the pulse wave detecting means on any other part of the same limb, such as a finger, so long as the part is located on the distal side of the cuff 10. Therefore, the apparatus may be adapted such that the pressure means is set on a femoral region and the pulse wave detecting means is set on a part of the same limb on the distal side of the pressure means.

Furthermore, the illustrated apparatus may be adapted to monitor the blood pressure of a subject, by determining (a) a relationship between blood pressure and pulse wave magnitude, based on at least one blood pressure value determined in the blood pressure measure routine (FIG. 2) and at least one magnitude of the probe pulse wave signal $SM_2$ supplied from the pulse wave probe 34, and (b) successively determining a systolic and a diastolic blood pressure of the subject, according to the determined relationship, based on a maximum and a minimum magnitude of each of successive pulses of the pulse wave signal $SM_2$ from the pulse wave prove 34.

It is to be understood that the present invention may be embodied with other changes, improvements, and modifications that may occur to those skilled in the art without departing from the scope and spirit of the invention defined in the appended claims.

What is claimed is:

1. An oscillometric-type automatic blood pressure measuring apparatus, comprising:

pressure means for pressing a body portion of a living subject with a pressure;

sensor means for detecting a pulse corresponding to a heartbeat of a living subject;

oscillometric-type blood pressure measuring means operating in each of a plurality of periodic measurement cycles, for (a) occluding an arterial vessel of said subject by increasing the pressure of said pressure means, (b) reading through said pulse sensor means, a series of pulses of a first pulse wave transmitted from said arterial vessel to said pressure means while reducing the increased pressure of said pressure means and (c) determining a first systolic blood pressure of said subject based on variation in amplitude of said series of pulses of said first pulse wave;

display means for indicating the first systolic blood pressure value measured by said oscillometric-type blood pressure measuring means;

pulse wave detecting means disposed downstream of said pressure means with respect to said arterial vessel, for detecting a series of pulses of a second pulse wave produced from a portion of said arterial vessel located downstream of said pressure means;

first determining means for determining, as an initial-pulse detection pressure, a pressure of said pressure means at a time when said pulse wave detecting means detects an initial pulse of said second pulse wave after said oscillometric-type blood pressure measuring means commences to reduce the pressure of said pressure means in said each measurement cycle;

second determining means for determining, in a current measurement cycle of said oscillometric-type blood pressure measuring means, a second systolic blood pressure of said subject based on an initial-pulse detection pressure determined by said first determining means in said current measurement cycle and at least one first systolic blood pressure measured by said oscillometric-type blood pressure measuring means in at least one measurement cycle prior to said current measurement cycle; and said display means for indicating the second systolic blood pressure value determined by said second determining means in said current measurement cycle, before said oscillometric-type blood pressure measuring means determines a first systolic blood pressure of said subject in said current measurement cycle.

2. The apparatus as set forth in claim 1, further comprising third determining means for determining a pressure difference between the initial-pulse detection pressure and the first systolic blood pressure which are determined and measured in said each measurement cycle, said second determining means determining in said current measurement cycle the second systolic blood pressure of said subject based on the initial-pulse detection pressure determined by said first determining means in said current measurement cycle and at least one pressure difference determined by said third determining means in said at least one measurement cycle prior to said current measurement cycle.

3. The apparatus as set forth in claim 2, wherein said second determining means determines in said current measurement the second systolic blood pressure of said subject by adding a pressure difference determined by said third determining means in a measurement cycle prior by one said cycle to said current measurement cycle, to the initial-pulse detection pressure determined by said first determining means in said current measurement cycle.

4. The apparatus as set forth in claim 2, wherein said second determining means comprises:
   identifying means for identifying a deviation of a pressure difference determined by said third determining means in a measurement cycle prior by one cycle to said current measurement cycle, from at least one pressure difference determined by said third determining means in at least one measurement cycle prior to said one-cycle prior measurement cycle; and
   adjusting pressure difference determining means for determining an adjustment pressure difference based on the identified deviation and at least one of the pressure difference determined in said one-cycle prior measurement cycle and the at least one pressure difference determined in said at least one measurement cycle prior to said one-cycle prior measurement cycle,
   said second determining means utilizing said adjustment pressure difference for determining, in said current measurement cycle, the second systolic blood pressure of said subject by adding said adjustment pressure difference to the initial-pulse detection pressure determined by said first determining means in said current measurement cycle.

5. The apparatus as set forth in claim 4, wherein said identifying means of said second determining means comprises:
   means for calculating an arithmetic means of a first predetermined number of pressure differences determined by said third determining means in a first predetermined number of measurement cycles prior to said one-cycle prior measurement cycle; and
   judging means for defining a deviation range having upper and lower limit values equal to a first and a second predetermined percentage of said arithmetic means, respectively, said first predetermined percentage being greater than 100%, said second predetermined percentage being smaller than 100%, said judging means identifying if the pressure difference determined by said third determining means in said one-cycle prior measurement falls within said deviation range;
   said adjustment pressure difference determining means of said second determining means determining, as said adjustment pressure difference for said current measurement cycle, an arithmetic means of the pressure difference determined in said one-cycle prior measurement cycle and said first predetermined number of pressure differences determined in said first predetermined number of measurement cycles prior to said one-cycle prior measurement cycle, when the pressure difference determined in said one-cycle prior measurement cycle is identified as falling within said deviation range.

6. The apparatus as set forth in claim 5, wherein said adjustment pressure difference determining means of said second determining means determines, as said adjustment pressure difference for said current measurement cycle, an arithmetic mean of the pressure difference determined in said one-cycle prior measurement cycle and the pressure difference determined in the measurement cycle prior by one cycle to said one-cycle prior measurement cycle, when the pressure difference determined in said one-cycle prior measurement cycle is identified as not falling within said deviation range and simultaneously when the pressure difference determined in said measurement cycle prior by one cycle to said one-cycle prior measurement cycle is identified as not falling within a preceding deviation range defined by said judging means such that an upper and a lower limit value of said preceding deviation range are equal to said first and second predetermined percentages, respectively, of an arithmetic mean of a first predetermined number of pressure differences determined by said third determining means in a first predetermined number of measurement cycles prior to said measurement cycle prior by one cycle to said one-cycle prior measurement cycle.

7. The apparatus as set forth in claim 5, wherein said adjustment pressure difference determining means of said second determining means determines, as said adjustment pressure difference for said current measurement cycle, the adjustment pressure difference determined thereby for said one-cycle prior measurement cycle, when the pressure difference determined in said one-cycle prior measurement cycle is identified as not falling within said deviation range and simultaneously when the pressure difference determined in said measurement cycle prior by one cycle to said one-cycle prior measurement cycle is identified as falling within a preceding deviation range defined by said judging means such that an upper and a lower limit value of said preceding deviation range are equal to said first and second predetermined percentages, respectively, of an arithmetic mean of a first predetermined number of pressure differences determined by said third determining means in a first predetermined number of measurement cycles prior to said measurement cycle prior by one cycle to said one-cycle prior measurement cycle.

8. The apparatus as set forth in claim 1, further comprising:
   means for determining a first pulse rate of said subject based on at least two successive pulses of said second pulse wave detected by said pulse wave detecting means before said oscillometric-type blood pressure measuring means commences to increase the pressure of said pressure means in said each measurement cycle;
   means for determining a second pulse rate of said subject based on (a) said initial pulse of said second pulse wave detected by said pulse wave detecting means after said oscillometric-type blood pressure measuring means commences to reduce the pressure of said pressure means in said each measurement cycle and (b) a pulse following said initial pulse; and judging means for defining a deviation range having upper and lower limit values equal to a first and a second predetermined percentage of said arithmetic means, respectively, said first predetermined percentage being greater than 100%, said second predetermined percentage being smaller than 100%, said judging means identifying if said second pulse rate falls within said deviation range, said second determining means utilizing said initial-pulse detection pressure for determining the second systolic blood pressure of said subject, when said second pulse rate is identified as falling within said deviation range, and discarding said initial pulse as a noise when said second pulse rate is identified as not falling within said deviation range.

9. The apparatus as set forth in claim 2, further comprising:

means for determining a first pulse rate of said subject based on at least two successive pulses of said second pulse wave detected by said pulse wave detecting means, before said oscillometric-type blood pressure measuring means commences to reduce the pressure of said pressure means in said each measurement cycle;

means for determining a second pulse rate of said subject based on (a) said initial pulse of said second pulse wave detected by said pulse wave detecting means after said oscillometric-type blood pressure measuring means commences to reduce the pressure of said pressure means in said each measurement cycle and (b) a pulse following said initial pulse; and judging means for defining a deviation range having upper and lower limit values equal to a first and a second predetermined percentage of said arithmetic means, respectively, said first predetermined percentage being greater than 100%, said second predetermined percentage being smaller than 100%, said judging means identifying if said second pulse rate falls within said deviation range, said third determining means utilizing said initial-pulse detection pressure for determining said pressure difference, when said second pulse rate is identified as falling within said deviation range, and discarding said initial pulse as a noise when said second pulse rate is identified as not falling within said deviation range.

10. The apparatus as set forth in claim 1, wherein each of said periodic measurement cycles lasts a predetermined interval of 5 to 10 minutes.

11. The apparatus as set forth in claim 1, wherein said pressure means comprises an inflatable cuff.

12. The apparatus as set forth in claim 1, wherein said pulse wave detecting means comprises:

a semiconductor pressure sensor having a press surface; and means for pressing said press surface of said pressure sensor against a wall of said downstream portion of said arterial vessel via skin tissue of said subject so as to partially flatten said wall.

13. The apparatus as set forth in claim 5, wherein said judging means defines said deviation range such that the upper and lower limit values of the deviation range are equal to 125% and 75% of said arithmetic means, respectively.

14. The apparatus as set forth in claim 8, wherein said judging means defines said deviation range such that the upper and lower limit values of the deviation range are equal to 125% and 75% of said first pulse rate, respectively.

* * * * *